(12) United States Patent
Petty et al.

(10) Patent No.: US 6,296,760 B1
(45) Date of Patent: Oct. 2, 2001

(54) DEVICE FOR THE REMOVAL AND CONCENTRATION OF IONIC METAL SPECIES FROM WATER

(75) Inventors: Jimmie D. Petty; William G. Brumbaugh; James N. Huckins; Thomas W. May; Raymond Wiedmeyer, all of Columbia, MO (US)

(73) Assignee: The United States of America as represented by the Secretary of the Interior, Washington, DC (US)

( * ) Notice: Subject to any disclaimer, the term of this patent is extended or adjusted under 35 U.S.C. 154(b) by 0 days.

(21) Appl. No.: 09/261,172

(22) Filed: Mar. 3, 1999

(51) Int. Cl.[7] ............................... C02F 1/28; C02F 1/62; B01D 17/00
(52) U.S. Cl. ..................... 210/170; 210/747; 210/634; 210/638; 210/688; 210/209; 210/502.1; 436/73; 436/80; 436/81; 73/61.42; 73/61.41
(58) Field of Search ..................... 210/747, 170, 210/644, 688, 634, 638, 502.1, 209; 436/73, 79, 80, 81, 178; 73/61.42, 61.41, 864.71

(56) References Cited

U.S. PATENT DOCUMENTS

| | | | |
|---|---|---|---|
| 4,092,117 | * | 5/1978 | Byrne . |
| 4,500,494 | * | 2/1985 | Scher . |
| 4,702,838 | * | 10/1987 | Babcock et al. . |
| 4,857,473 | * | 8/1989 | Magaritz et al. . |
| 4,874,405 | * | 10/1989 | Minhas . |
| 5,087,372 | * | 2/1992 | Toyomoto et al. . |
| 5,098,573 | * | 3/1992 | Huckins et al. . |
| 5,100,555 | * | 3/1992 | Matson . |
| 5,110,473 | * | 5/1992 | Hassett . |
| 5,395,426 | * | 3/1995 | Huckins et al. . |
| 5,618,433 | * | 4/1997 | Tarbet et al. . |
| 5,834,633 | * | 11/1998 | Davison . |

FOREIGN PATENT DOCUMENTS

96/30739 * 10/1996 (WO) .

* cited by examiner

Primary Examiner—Thomas M. Lithgow
(74) Attorney, Agent, or Firm—E. Philip Koltos

(57) ABSTRACT

A device is provided for capturing ionic metal species (e.g., Cd, Cu, Ni, Pb and Zn) dissolved in water. The device includes a nonporous polymeric tube for capturing the dissolved ionic metal species. The tube is formed from a membrane having transient cavities therein having an average pore size greater than 10 Å. A sequestration medium, contained within the tube, transforms the ionic metal species captured by the tube into a complexed, non-mobile metal species. The sequestration medium is capable of diffusing through the nonporous polymeric membrane at a controlled rate to form the complexed, non-mobile species and can comprise a mixture and metal complexing agent (e.g., a quinoline) and a long chain organic acid (e.g., oleic acid).

20 Claims, 2 Drawing Sheets

DEVICE FOR THE REMOVAL AND CONCENTRATION OF IONIC METAL SPECIES FROM WATER

FIELD OF THE INVENTION

The present invention relates to devices for capturing and removing ionic metal species from water and for concentrating the species after removal for analysis and other purposes.

BACKGROUND OF THE INVENTION

Global emissions of toxic metal residues to a wide spectrum of aquatic ecosystems have increased dramatically over the past 100 years due primarily to anthropogenic releases associated with mining, metal refining operations and industrial activity. Closely associated with these increases in the release of metal residues into the environment is the widespread increase in the concentrations of metals in fish, wildlife and human populations. Associated with this increase in exposure to metal residues is a wide variety of toxic responses ranging from reproductive problems to impaired mental development. In addition to aqueous exposure, movement of metal contamination up food chains can lead to contamination of wildlife and humans not directly exposed to metal pollution. The increasing industrialization on a global scale will be accompanied by an escalating demand for metals and a subsequent rise in metal waste discharges into aquatic systems. Monitoring of toxic metal species, potentially impacting wildlife and humans, and remediation of metal contamination will be critical activities for the foreseeable future.

Laboratories conducting analytical and toxicological research concerning the presence and toxicity of metal species must have sampling and analytical methods capable of defining the presence and amounts of bioavailable metal residues. In general, current sampling methods are not integrative over sufficient time intervals to sequester adequate amounts to detect trace to ultra-trace levels of metal residues (many of which may have toxicological significance) and to cost effectively detect episodic releases. Also, current sequestration methods are not adequate for integratively isolating sufficient amounts of the mixtures of toxic metals present in aquatic systems for use with bioassay procedures or for toxicity testing.

Considering the prior art in more detail, although there has been considerable effort directed towards development of methods for removing heavy metals from highly contaminated industrial and mining waste streams, relatively little has been accomplished in the development of a complementary monitoring device for trace level metals. The sequestration approaches which have been previously developed for the cleanup of metal waste streams are generally ineffective for the low (part per billion to part per trillion) concentrations present in natural waters. In addition, all of these approaches are impractical for application with long-term, unattended monitoring of metal residues in remote aquatic systems. Integrative sampling for low concentrations of metals has yet to be rigorously demonstrated.

Patents of interest in this general field include the following U.S. Pat. No. 4,303,702 (Courduvelis et al); U.S. Pat. No. 4,500,494 (Scher); U.S. Pat. No. 4,702,838 (Babcock et al); U.S. Pat. No. 5,037,555 (Pasternak et al); U.S. Pat. No. 5,087,372 (Toyomoto et al); U.S. Pat. No. 5,190,660 (Lindoy et al); U.S. Pat. No. 5,316,683 (Haesebroek; et al); U.S. Pat. No. 5,616,533 (Tavlarides et al); U.S. Pat. No. 5,618,433 (Tarbet et al); U.S. Pat. No. 5,668,079 (Tavlarides et al); U.S. Pat. No. 5,738,791 (Schomaker et al); U.S. Pat. No. 5,814,226 (Tavlarides et al); U.S. Pat. No. 5,817,289 (Tavlarides et al); and U.S. Pat. No. 5,834,633 (Davison). Briefly considering some of these references the Davison patent discloses a probe device for use in measuring quantities of a component in a liquid environment, which comprises (1) a membrane which is permeable to the component and (2) a layer of a material capable of binding the component and arranged to receive material which has permeated through the membrane from a face thereof juxtaposed to the fluid environment. The membrane is a polyacrylamide gel, and the material for binding the component may be a particulate material and may be incorporated in the membrane or provided as a separate layer juxtaposed thereto. The material comprises an immobilized complexing agent. This device can be used for determining quantities of trace metals in an aqueous environment. The Schomaker et al patent discloses a method for extracting metal ions from an aqueous solution comprising contacting the aqueous solution with particles of a hydrophobic, isotropic, microporous polymer in which there is immobilized an organic complexing agent selected from the group consisting of organic carboxylic acids, organic phosphorus compounds, oxime compounds and mixture thereof. The Lindoy et al patent teaches a method of removing preselected metal ions from solution by complexing them with an immobilized polyethylnimine. The Babcock et al patent discloses a method for the selective removal of metal ions (e.g., copper) from a plating solution (e.g., a nickel plating solution) comprising contacting the plating solution with liquid organic complexing agents such as oximes or phosphoric acid esters or using a microporous material impregnated with such substances and in the form of gels, sheets and beads. The gel is coated onto a solid microporous support, and the support itself contains the complexing agent. The Scher patent provides a process for the purification of an aqueous solution containing metal ion impurities. The process comprises contacting the solution with a plurality of polyurea and urea-formaldehyde microcapsules which enclose a chelating agent selected from $\beta$-diketones, 8-hydroxyquinolines and their thiol analogs, and oximes. The remaining patents further illustrate the state of the art.

SUMMARY OF THE INVENTION

An object of the present invention is to provide a passive integrative sampler device suitable for long-term (e.g. at least 28 days), low-level monitoring of potentially toxic trace metals such as cadmium (Cd), copper (Cu), nickel (Ni), lead (Pb), and zinc (Zn), each of which is most toxic in the "free" dissolved, i.e., readily bioavailable, state.

In accordance with a preferred embodiment of the invention, a device is provided for removing and concentrating ionic metal species from water, the device comprising: a nonporous polymeric membrane for capturing ionic metal species dissolved in water; and a hydrophobic sequestration medium contained by the membrane for transforming the ionic metal species captured by the membrane into a complexed, non-mobile metal species.

In general, the hydrophobic sequestration media comprises a sequestration medium capable of diffusing through the polymeric membrane at a controlled rate and capable of forming the complexed, non-mobile metal species. The sequestration medium preferably comprises a mixture of a metal complexing agent and a long chain organic acid. Advantageously, the complexing agent comprises a complexing agent selected from the group consisting of quinolines, dithiocarbamates, polyamines, iminodiacetate, polyketones, and thiols, and said organic acid comprises an organic acid selected from the group consisting of oleic acid, steric acid, eladic acid, linoleic acide, and linolenic acid. In a specific beneficial implementation, the complexing agent comprises alkyl substituted 8-hydroxy quinolines, and in a more specific implementation, the quinolines comprise 7-(4-ethyl-1-methyloctyl)-8-hydroxy quinoline and the organic acid comprises oleic acid.

In a preferred embodiment, the nonporous membrane forms a sealed tube and the sequestration media is contained within the tube. Advantageously, the tube comprises a flattened tube. In an implementation providing additional strength, a microporous polymer surrounds the tube formed by the nonporous membrane tube. The nonporous polymeric membrane preferably comprises a nonporous synthetic polymer selected from the group consisting of polyethylene, polypropylene, silicone, polyvinylchloride, chlorinated polyethylene, chlorosuphonated polyethylenes, polyimides, and polyethylene vinylacetate copolymers. Advantageously, the membrane has a thickness between 2 and 500 $\mu$m.

In an advantageous implementation, the tube further comprises a sheath for permitting movement of water and associated ionic metal species to membrane surface sites at which reaction with the sequestration phase occurs while limiting water flow past these membrane surface sites. Preferably, the sheath comprises a hydrophilic polymer membrane. Advantageously, the sheath comprises a hydrophilic membrane selected from the group consisting of cellulose dialysis membranes, and hydrophilic polypropylene, polyvinylidene fluoride and polyether sulphone polymer membranes.

According to a further aspect of the invention, a device is provided for removing and concentrating ionic metal species from water, the device comprising: a nonporous polymeric tube for capturing ionic metal species dissolved in water, the tube being comprised of a membrane having a transient cavities therein having average size no greater than 10 Å; and a sequestration medium contained within the tube for transforming the ionic metal species captured by the tube into a complexed, non-mobile metal species, the sequestration medium comprising a medium capable of diffusing through the nonporous polymeric membrane at a controlled rate and of forming the complexed, non-mobile species. As indicated above, the sequestration medium preferably comprises a mixture of a metal complexing agent and a long chain organic acid, and, advantageously, the complexing agent comprises a complexing agent selected from the group consisting of quinolines, dithiocarbamates, polyamines, iminodiacetate, polyketones, and thiols, and the organic acid comprises an organic acid selected from the group consisting of oleic acid, steric acid, eladic acid, linoleic acide, and linolenic acid. In one preferred implementation, the device further comprises a microporous polymer surrounding the tube formed by the nonporous membrane, while in another, the device further comprises a sheath for permitting movement of water and associated ionic metal species to membrane surface sites at which reaction with the sequestration phase occurs while limiting water flow past these membrane surface sites.

Other features and advantages of the invention will be set forth in, or apparent from, the following detailed description of preferred embodiments of the invention.

DESCRIPTION OF THE PREFERRED EMBODIMENTS

Figure 1:
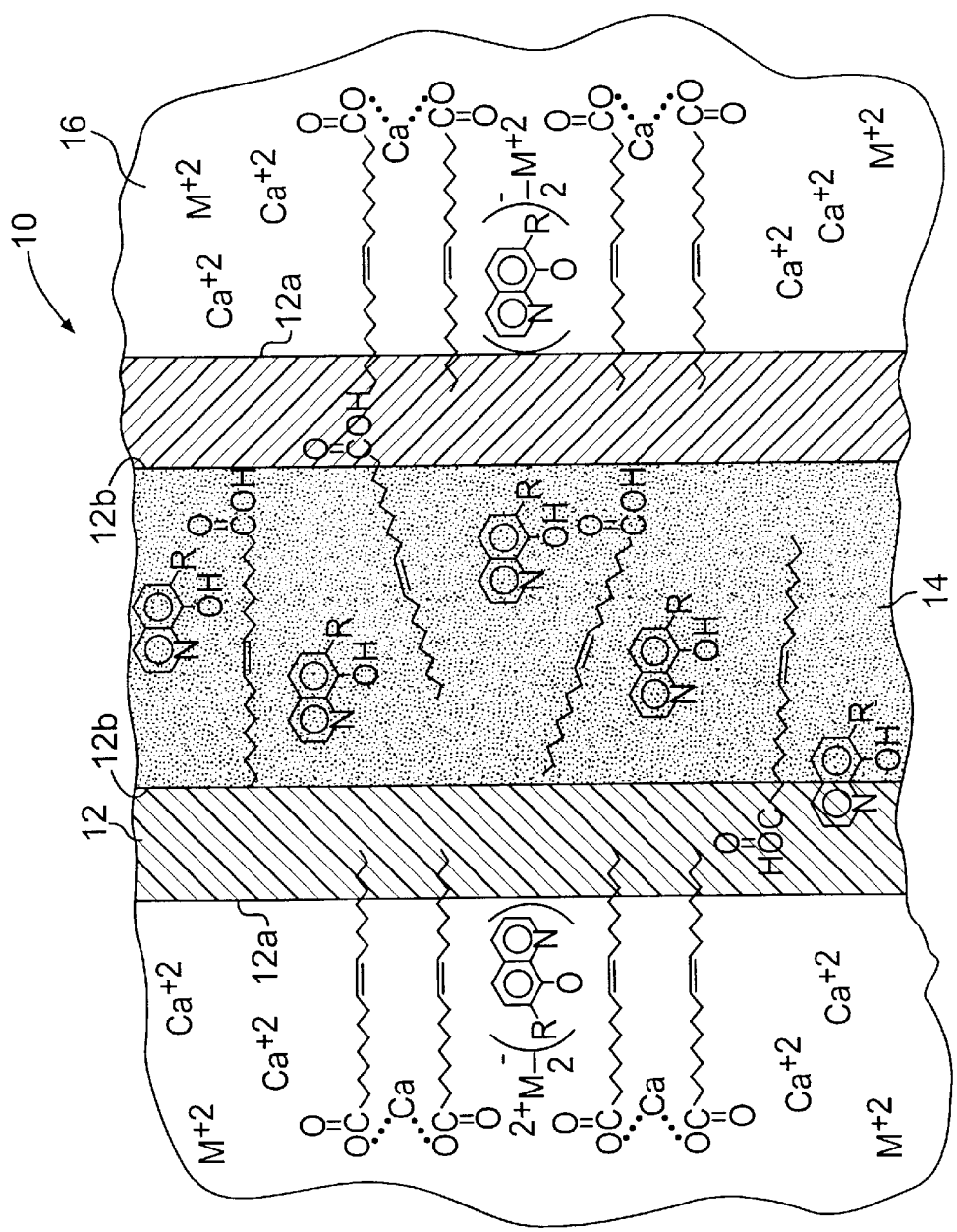
FIG. 1 is a highly schematic cross sectional view of a first preferred embodiment of the invention.

As indicated above, generally speaking, the present invention comprises a sealed nonporous polymeric tube containing a mixed sequestration phase capable of transforming a dissolved ionic metal species into a non-mobile (complexed) species which will accumulate in the device. Referring to FIG. 1 of the drawings, there is shown, in a highly schematic manner, a sampler device in accordance with the invention. The device, which is generally denoted 10, comprises a tubular hydrophobic polymeric membrane 12, the outer surfaces of which are indicated at 12a and the inner surfaces of which are indicated at 12b. In the specific embodiment under consideration, the device 10 contains, sealed in an interior space 14 thereof, a hydrophobic reagent comprising carboxylic acid (e.g., oleic acid) and alkylated 8-hydroxyquinoline (R=akyl group with 8 to 21 carbons). Outside of the membrane is the aqueous sampling medium 16 which contains the ionic metals to be sampled. In this specific embodiment, a calcium ion ($Ca^{+2}$) and an analyte metal ion ($M^{+2}$) are shown. The metal ion sequestration process indicated schematically in FIG. 1 is described in more detail below.

Figure 2:
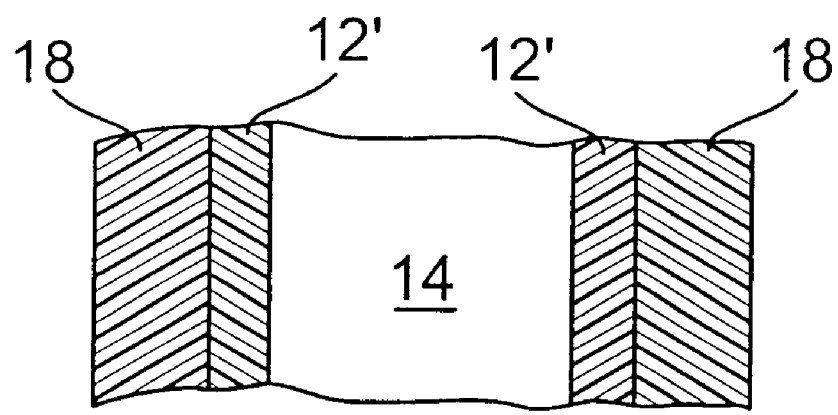
FIG. 2 is a highly schematic cross sectional view of a further preferred embodiment of the invention.

The polymeric tube 10 is preferably made of thin-walled nonporous polyethylene, polypropylene, polyvinyl chloride, silicone, or the like. In an alternative embodiment illustrated in FIG. 2, a thin layer of a nonporous polymer, indicated at 12, 12' can be grafted or laminated to a thicker microporous polymer layer, demoted 18 such as microporous polypropylene, to increase strength and increase release (membrane) rates of the sequestration media.

The nonporous membranes used in the present invention are generally characterized by liquid-like and solid regions of the polymer, and have no air filled fixed pores, but rather have transient cavities in the liquid-like regions. The size of these transient cavities in the nonporous polymers are extremely small (usually $\leq$10 Å in cross sectional diameter) and thus the membrane usually limits the rate of chemical release. These nonporous polymers are hydrophobic in nature and are virtually non-permeable to charged or polar species. Consequently, water as either vapor or liquid will not pass through the transient cavities. In contrast, neutral organic species employed as complexing agents for ionic metals are often hydrophobic and will readily permeate nonporous polymers and make contact with the water insoluble sequestration phase. Because the sequestration phase will chelate freely dissolved ionic metals, and only dissolved ionic metal species are readily bioavailable, the device of the invention provides a more realistic estimate of organism exposure to toxic metal residues.

As discussed above, in general, the sequestration phase comprises a mixture of a metal complexing agent and a long chain organic acid capable of rendering a broad spectrum of dissolved ionic metal species into a non-mobile complexed form. Examples of such complexing agent mixtures include that discussed in conjunction with FIG. 1, i.e., more specifically, a mixture of alkyl substituted 8-hydroxy quinolines, specifically 7-(4-ethyl-1-methyloctyl)-8-hydroxy quinoline, and a long chain organic acid, specifically oleic acid. In addition to these examples, complexing agents such as dithiocarbamates, polyamines, iminodiacetate, polyketones, and thiols combination with organic acids such as steric acid, eladic acid, linoleic acid, and linolenic acid, as well as other complexing agents, can be employed to sequester the ionic metal species from water. In general, any hydrophobic sequestration media which will diffuse through the polymeric membrane at a controlled rate and which is capable of forming complexed non-mobile metal species can be employed as the sequestration phase of the present invention.

The major driving force for uptake of dissolved ionic metals from water, when the device of the invention (i.e., a device containing a mixture of hydrophobic liquid complexing agents in a polymeric membrane) is deployed in aquatic systems, is a steep concentration gradient. This results from the controlled release of the liquid complexing mixture to the surface of the nonporous polymeric membrane and the subsequent reaction of the dissolved ionic metals with the water insoluble organic phase to form very stable metal chelates with high binding constants and extremely low water solubility. Reaction of the dissolved metals with the sequestration phase results in the formation of non-mobile complexed forms of the ionic metals in a water insoluble organic matrix. The release of the sequestration phase from the interior of the device to the surface of the non-porous membrane is controlled by permeation of the liquid complexing agents through the hydrophobic membrane. Further, the kinetically controlled selective reaction of the long chain organic acid (e.g., oleic acid) with divalent calcium present in all natural waters results in a waxy surficial deposit into which fresh sequestration media continually diffuses thereby producing a stabilized liquid membrane with a continually replenished reactive surface. This transformation effectively removes metal species (infinite sink) from one media and concentrates the transformed metal species form in a second, isolated media. Because of this process, the aforementioned metal species are concentrated in a linear manner through time. For example, in laboratory experiments it was determined that the uptake rate remained constant during a twenty-eight (28) day exposure. For a 20 $\mu$g/L exposure, the uptake rates for the five test metal ions ranged from 40 to 50 ng/day per $cm^2$ surface area of the device. Also, if devices of sufficient size or numbers are exposed to closed or low exchange rate environments, the metal removal rate should be great enough to lower the overall concentration of ionic metal species. Longer exposure times will result in higher concentration factors above ambient levels.

After concentration, the immobilized metal species are analyzed. This analytical determination of the immobilized metal residues, and recovery and analysis of the complexed metal species, can be accomplished using widely recognized standard techniques (e.g., digestion, atomic absorption spectroscopy, inductively coupled plasma mass spectrometry, and the like). In this regard, any enrichment procedure or analytical technique applicable to measuring ionic or complexed metal species is suitable for determining metal concentrations sequestered by the present invention.

Turning now to a consideration of the range of possible configurations and process parameters for sequestration of ionic metal species from water, these include those suitable for small scale (analytical) processing to those useful in larger industrial or remedial scale processing. As indicated above, a variety of types of nonporous synthetic polymeric films can theoretically be used in making the device. A more complete listing includes polyethylene, polypropylene, silicone and Silastic®, polyvinylchloride, chlorinated polyethylene, chlorosulphonated polyethylenes, polyamides, polyethylene vinylacetate copolymers, laminates of microporous polymers with these nonporous polymers, and the like. The test results discussed below were generated using polyethylene. However, each of the above polymers (and perhaps others as well) should be effective. Relatively thin polymeric films of 0.0001 to 0.0196 inches (2 to 500 $\mu$m) thickness are generally better suited for all applications because of the need to maximize transport of the neutral organic sequestration media through the polymeric membrane. However, for greater strength, industrial or large-scale applications should be constructed of thick polymeric membranes to safely hold larger amounts of the sequestration media. Further, alternative approaches such as that discussed above in connection with FIG. 2 can also be used.

In most cases, the membrane of the device of the invention controls the transport of the neutral complexing agent mixture to the surface of the polymeric membrane and also controls the time to saturate the device. Saturation completes the uptake process and requires replacement by another device(s) if monitoring or cleanup is continued. In general, increasing film thickness of nonporous polymers to increase the strength of the device reduces permeation or sequestration rates (typically in a linear manner at constant temperature and pressure) of neutral chemicals through nonporous synthetic polymers. A film thickness of $\leq 100$ $\mu$m is recommended for small scale ($\leq$mL volumes of the sequestration phase) analytical applications of the present invention. However, applications such as the use of large volumes of organic hydrophobic complexing agents enclosed in high surface area polymeric films for removal of dissolved ionic metals from various situations may require the greater strength and durability of the upper range of film thickness, i.e., 100 to 500 $\mu$m. In addition, for hydrocarbon polymers such as polyethylene or polypropylene, properties of low density, low crystallinity, and low chain orientation may be desirable because these properties maximize transport of neutral chemicals through the film matrices, thereby effectively enhancing the formation of the stabilized liquid membrane.

The ratio of surface area (polymer film) to volume (enclosed complexing media) used with the present invention can vary greatly depending on the nature of the particular application for the device. The larger surface area configurations permit greater total permeation of complexing chemicals to the surface of the polymeric membrane per unit time, which increases ionic metal removal. Such configurations are typically employed in analytical applications. For some large scale or remedial applications, adequate rates of removal of dissolved ionic metals may require large numbers or long lengths of tubing (with the exact design requirements to be determined in pilot studies) containing large amounts of the complexing agents. An example of a large scale configuration is as follows: approximately 2000 mL of an equal volume mixture of 7-(4-ethyl-1-methyloctyl)-8-hydroxy quinoline and oleic acid (cis-9-octadecenoic acid) is placed in a three meter length of 15 centimeter wide, low density polyethylene tubing having a wall thickness of 0.01 to 0.03 centimeters. The tubing used is "layflat,", i.e., flattened, tubing, and the ends of the layflat tubing are heat sealed, secured with large clamps, or the like, and placed in the water of interest. The device so configured can be deployed in multiple single large-scale configuration arrays or in cluster arrays.

It will be appreciated that by employing many of these complexing agent containing systems, the contaminated water of interest can be exposed to large amounts of the transformation media for adequate removal of ionic metals.

In addition to the examples set forth above, the sequestration phase can also comprise a mixture of two or more complexing agents, one of which will form water insoluble salts with alkaline earth metal ions. Examples of such complexing agents are 8-hydroxyquinoline, alkyl substituted 8-hydroxyquinolines, dithiocarbamates, polyamines, iminodiacetate, polyketones, thiols, steric acid, eladic acid, linoleic acid, linolenic acid, oleic acid, and the like. As indicated above, in general, any hydrophobic sequestration media which will diffuse through the polymeric membrane at a controlled rate and which is capable of transforming dissolved ionic metal species into non-mobile complexed forms can be employed as the sequestration phase of the device of the present invention.

It is noted that the maximum capacity of the enclosed hydrophobic organic complexing media for removing ionic metals is determined by the sequestration phase volume and the nature of the sequestration medium. For example, the capacity of the alkyl substituted 8-hydroxy quinoline employed in one embodiment of the invention for complexing divalent copper can be readily calculated from the formula weight (308) and specific gravity (0.99 g/mL) of the substituted quinoline and the fact that the binding ratio is 2:1 for a divalent metal. Thus, the equivalent weight of the complexing reagent is 616 g/equivalent and one (1) mL contains 0.99 g÷616=0.00161 equivalents or 1.6 mequivalents. For copper (63 mg/mequivalent) the capacity of the invention is 63×1.61=101.4 mg/mL. In the case of the large-scale device described above, the 1000 mL of the alkyl substituted 8-hydroxyquinoline would sequester 100,000 mg (100 g) of copper. Similar calculations can be used to determine the capacity of the invention for other divalent metal ions.

With respect to the effects of pH and flow rates on the sequestration of soluble ionic metal species by the device of the invention, significant extraction of Ni, Cu, Zn, and Pb has been accomplished at pHs as low as 5.8. Cadmium was not significantly extracted below a pH of 6. At circumneutral pHs, all of the toxic metals were quantitatively sequestered by the complexation media. Because nearly all natural waters range from pH 6 to 9, the invention will be applicable for sequestering readily bioavailable ionic metals from a wide array of ambient waters.

Water flow rates are also an important factor potentially affecting the sequestration rate of ionic metals by the stabilized liquid membrane sampling device of the invention. Because the reaction to form a non-mobile complexed form of ionic metal residues occurs at the surface of the polymeric membrane, the thickness of the aqueous boundary layer at the water/membrane or device interface affects the overall sampling rate for sequestration of metal residues. This boundary layer is essentially the layer where the concentration of ionic metal ions is depleted relative to the bulk solution concentrations. Replenishment occurs at a rate dependent on the diffusion of ions from the bulk of the solution (see Zhang, H.; Davison, W., Performance Characteristics of Diffusion Gradients in Thin Films for the In Situ Measurement of Trace Metals in Aqueous Solution, Anal. Chem., 1995, 67,3391-3400). The effect of the boundary layer on sampling rates is dependent on ion mobility, temperature, and hydrodynamics of the water around the membrane surface. For static exposures (or deployment of the invention in quiescent aquatic systems), the boundary layer would be considerably thicker than for a flowing water system or stirred water exposure. A sampling rate for a static exposure is typically calculated from the slope of the uptake curve during the initial phase of the exposure (see Huckins, J. N.; Manuweera, G. K., Petty, J. D.; MacKay, D.; Lebo, J. A. Lipid-containing Semipermeable Membrane Devices for Monitoring Organic Contaminants in Water, Environ. Sci. Technol., 1993, 27, 2489–2496) because the water concentration, and subsequently the measured uptake rate, is continually decreasing. In testing that has been performed, the static exposure sampling rate was taken as the uptake rate for the time interval over which the initial water concentration was reduced by 25%. Thus, the static exposure (or quiescent deployment) case sampling rate for a 15 cm long by 2.54 cm wide device (at pH 7.5 and 22° C.) was determined to be 0.154 L/d.

The diffusional boundary layer is minimized by stirred or flowing water exposures. In the testing in question, the devices were exposed in a stirred water system at pHs of 6.0 and 7.5. The sequestration of the ionic metals by the devices was determined through time (i.e., 0,1, 2, 4, 8, 24, 48, 72, and 144 hours). To ensure that the sequestration of metal ions was in the linear phase, the sampling rates were determined from the curve representing the first 25% of metal uptake. This linear portion was extrapolated to the x-axis to determine the time required to sample the entire 1.8 L exposure volume. This value was converted into an L/d sampling rate. The sampling rates in an exposure for which the boundary layer is minimized by rapid stirring are given in Table 1 below. As is readily seen, the sampling rates for sequestration of the metal ions increased significantly for stirred water with sampling rates at pH 7.5 being greater than 10 L/d for Cu, Ni, and Zn and 6 Ud for Cd and 3 L/d for Pb. These sampling rates are indicative of those expected under flowing water conditions.

TABLE 1

Estimated Sampling rates for sampler devices in simulated freshwater at two pHs (with stirring).
Estimate Sampling Rate (liter-equivalents/day)

| pH | Ni | Cu | Zn | Cd | Pb |
|---|---|---|---|---|---|
| 6.0 | 10.8 | 10.8 | 7.2 | 1.8 | 1.8 |
| 7.5 | 10.8 | 10.8 | 10.8 | 6.2 | 3.0 |

Figure 3:
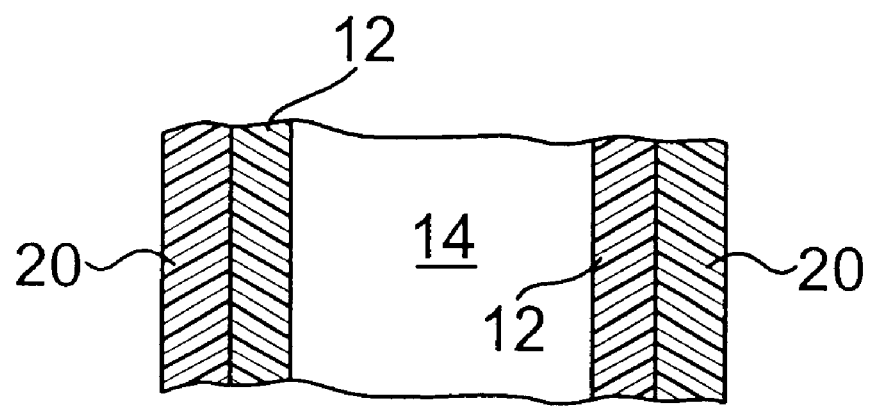
FIG. 3 is a highly schematic cross sectional view of yet another embodiment of the invention.

In an alternative embodiment illustrated in a highly schematic manner in FIG. 3, in order to reduce the effects of variable flow across the surface of the device of the invention, a hydrophilic sheath, denoted 20, is provided for membrane 12. This is especially advantageous for applications where time-weighted, integrated water concentrations are to be estimated in flowing waters. The hydrophilic material of sheath 20 allows movement of water and associated ionic metal species to the surface of the membrane 12 where reaction of the metal residues with the sequestration phase occurs while limiting the flow of water past the reactive surface. Materials such as cellulose dialysis membranes with molecular weight cutoffs≦1000, hydrophilic polypropylene, polyvinylidene fluoride, polyethersulfone, and other hydrophilic polymeric membranes may be used as a sheath material for the device of the invention. In general, any polymeric material which will allow controlled diffusion of the ionic metal species of interest to the reactive surface of the device, while limiting the diffusion of particulate material, colloids, and biogenic polymers such as humic and fulvic acids will function as a sheath for the device.

A further advantage of incorporation of a flow limiting sheath material, such as that indicated schematically at 20 in FIG. 3, is in providing more reproducible sampling rates for sequestration of ionic metals by the device of the invention. For example, in prior testing, membrane sampling devices on both sheathed and non-sheathed configurations were employed at two sites (designated A68 and A72) in the upper Animas River in Colorado for nine days. Both sites contain elevated metals concentrations; however, colloid-size precipitates were more evident at the A72 site. Samples were taken on days 3, 5, and 9 of the deployment. The devices were sheathed using cellulose dialysis membrane with a 1000 molecular weight cutoff. The dialysis membrane was pre-extracted with acid to remove any metal contamination prior to preparation of the devices. The results of the analysis of these samples are given in Table 2 below. In both types of samplers, the metal residues sequestered increased during the field exposure, with the non-sheathed devices generally sequestering greater amounts of metals. However, this trend was not universal. At deployment site A72, considerably more Cd, Ni, and Zn were sequestered by the sheathed devices, whereas for Cu and Pb, the opposite was true. The effects of particulate bound and colloidal associated metals on the sequestration of metal residues by the non-sheathed devices is presently unknown. In the case of the sheathed devices, a generally linear uptake of the target metals was observed. Also, the sampling rates calculated for the two configurations from this field deployment are presented in Table 3 below. Sampling rates for the sheathed devices ranged from 0.09 (Cd, site A72) to 0.034 (Zn, site A68) L-equivalents/d, while sampling rates for the non-sheathed devices ranged from 0.02 (Cd, A72) to 15.6 L-equivalents/d. Sampling rates were significantly more consistent for the sheathed configuration. In most cases, the sampling rates for the ionic metals observed for the sheathed devices were similar to the value of 0.15 L-equivalents/d measured in laboratory exposure experiments (see above). Consequently, the cellulose sheath not only eliminated the uptake of colloidal and particulate associated metal residues, but also served to control flow of water to the reactive surface of the devices. Incorporating a sheathed configuration will enhance the effectiveness of the device of the invention for use in determining the ambient concentrations of toxic metals in aquatic systems. Employing the non-sheathed configuration of the device allows a determination of the possible effects of colloidal and particulate associated metal residues and for removal of all labile forms of ionic metals.

TABLE 2

Mass (in µg) of Ni, Cu, Zn, Cd and Pb recovered from sampler devices deployed for 3, 5, and 9 days at two sites on the upper Animas River, CO.
Mass of Sequestered Analyte (µg)

| Site-Day | SLMD Type | Ni | Cu | Zn | Cd | Pb |
|---|---|---|---|---|---|---|
| A68-3 | sheathed | 0.71 | 1.00 | 277 | 0.58 | 0.30 |
| A68-5 | sheathed | 1.31 | 1.77 | 660 | 1.48 | 0.36 |
| A68-9 | sheathed | 2.16 | 3.71 | 1230 | 2.71 | 0.94 |
| A-68-3 | unsheathed | 2.37 | 14.0 | 1110 | 0.34 | 4.34 |
| A68-5 | unsheathed | 3.46 | 22.6 | 1630 | 0.61 | 15.6 |
| A68-9 | unsheathed | 4.98 | 60.7 | 2740 | 1.84 | 120 |
| A72-3 | sheathed | 2.51 | 4.00 | 309 | 0.42 | 0.21 |
| A72-5 | sheathed | 3.71 | 6.00 | 454 | 0.53 | 0.16 |
| A72-9 | sheathed | 4.91 | 9.32 | 655 | 0.87 | 0.19 |
| A72-3 | unsheathed | 1.75 | 50.1 | 44 | 0.20 | 2.30 |
| A72-5 | unsheathed | 2.22 | 81.0 | 63 | 0.15 | 2.49 |
| A72-9 | unsheathed | 2.62 | 122 | 94 | 0.18 | 4.63 |

TABLE 3

Estimated sampling rate[a] for SLMDs deployed at two sites in the upper Animas River, CO.
Estimate Sampling Rate (liter-equivalents/day)

| Site-configuration | pH[b] | Ni | Cu | Zn | Cd | Pb |
|---|---|---|---|---|---|---|
| A68-sheathed | 6.9 | 0.17 | 0.11 | 0.34 | 0.26 | 0.12 |
| A72-sheathed | 6.6 | 0.21 | 0.28 | 0.22 | 0.09 | 0.09 |
| A68-unsheathed | 6.9 | 0.40 | 1.76 | 0.76 | 0.18 | 15.6 |
| A72-unsheathed | 6.6 | 0.11 | 3.65 | 0.03 | 0.02 | 2.26 |

[a]Sampling rate based on average filtered water concentration collected over 9 days (n = 4).
[b]Initial pH.

With respect to the effects of temperature on the diffusion of the hydrophobic organic complexing agents through the non-porous polymers of the device of the invention, it is surmised, by analogy to the increase in permeation rates observed for a variety of neutral organic molecules (see Huckins, J. N.; Petty, J. D.; Lebo, J. A.; Orzaio, C. E.; Prest, H. F.; Tillitt, D. E.; Ellis, G. S.; Johnson, B. T.; Manuweera, G. K. Semipermeable Membrane Devices (SPMDs) for the Concentration and Assessment of Bioavailable Organic Contaminants in Aquatic Environments: *Techniques in Aquatic Toxicology*, Ed., G. K. Ostrander, CRC Lewis Publishers, Boca Raton, Fla., 1996, pp 625–655) that an increase in temperature can be expected to result in an increase in the amount of sequestration media diffusing to the membrane surface. Temperature is not a constraint unless the sequestration phase freezes at the temperature of application.

In alternative embodiments of the invention, the device described above can comprise both small and large diameter polymeric tubing, as well as partly sealed polymeric film sheets which provide a very large surface area, and these can be arranged in bundles or arrays, and the like, secured by means of a frame or other deployment arrangement, filled with the appropriate sequestration phase, and subsequently sealed. Thereafter, these configurations can be placed in contaminated water systems where the water moves or is forced by the arrays and makes intimate contact with the device so as to provide an active sampling regimen for removing and concentrating ionic metal species. As described above, such an arrangement can be employed for analytical purposes or used on an industrial or remediation scale.

Turning to some of the advantages of the invention over existing approaches for sequestering ionic metal species, these advantages include greater simplicity, reliability (i.e., the device is not prone to mechanical problems or breakdowns), enhanced analytical precision for measurements of bioavailable ionic metal residues, improved detection limits for toxic metal residues, wider applicability especially in remote, unattended situations, and substantial cost savings. In addition, the device of the invention samples the most biologically available metal species, thus providing an estimate of organism exposure. As a result, the invention provides the best estimate of the presence and potential biological significance of exposure to toxic metals in a time weighted integrative manner.

As discussed above, the invention has been demonstrated to be highly efficient and effective for removing and concentrating ionic metal residues for up to at least 28 days. No other approach has been demonstrated to be effective for periods greater than 7 days. An important feature of the invention is that the ionic metal is sequestered thereby and transformed into a non-mobile form in a stabilized liquid membrane media that can be easily and directly analyzed by the most widely employed analytical methods. Therefore, extensive laboratory processing steps, with the accompanying potential for contamination of the sample, are minimized. This results in improved detection limits and analytical precision, especially for laboratories which do not routinely conduct sample preparation and analysis using high-cost clean room conditions and procedures. Also, the present invention is more widely applicable to monitoring studies than any existing art primarily because it has much higher sampling rates (even based on the small laboratory design cited earlier), and can be used in an integrative manner for weeks due to the transformation of the ionic metal species into a non-mobile, complexed form in the device. The stability of metal residues collected by any prior art method is much less certain and is often problematic.

The present invention also provides a basis for a cost effective, efficient remediation system applicable to effluent streams, mine drainage, and hazardous waste leachates. Because the toxic metals are transformed into a non-mobile form and because the invention can be configured into large-scale arrangements, it is possible to deploy the sampling device of the invention as a treatment for removal of a wide variety of ionic metals. The sequestered metals are easily recovered for ultimate disposal or recycling. It is believed that no other current approach for isolating metals is as simple, effective and applicable to as wide a variety of aquatic systems.

The principal application of the invention is in monitoring the average exposure of humans and other living things to water borne ionic metal specie. The device of the invention is a very valuable tool for defining the source, transport, and rate/deposition of toxic metal residues. Further, because of integrative sampling provided thereby, the device is applicable to the reduction of metal species in aquatic systems of limited areal extent. The invention will be very useful to resource managers, regulators, and scientists responsible for determining the impact of chemicals on fish and wildlife resources and human health. The device enables the measurement of the amounts of metal residues present in a broad array of aquatic systems, prediction of their potential adverse effects, and in some cases remediation of unacceptably high levels. In brief, government agencies, private sector personnel and members of the scientific community involved in monitoring/regulating environmental contaminants, specifically metal species, will have extensive application for this invention.

Although the invention has been described above in relation to preferred embodiments thereof, it will be understood by those skilled in the art that variations and modifications can be effected in these preferred embodiments without departing from the scope and spirit of the invention.

What is claimed is:

1. A device for removing and concentrating ionic metal species from water, said device comprising:
    a nonporous polymeric membrane for capturing on an external surface thereof ionic metal species dissolved in water; and
    a hydrophobic sequestration medium contained by said membrane for transforming the ionic metal species captured by said membrane into a complexed, non-mobile metal species.

2. A device as claimed in claim 1 wherein said hydrophobic sequestration media comprises a sequestration medium capable of diffusing through the polymeric membrane at a controlled rate and of forming said complexed, non-mobile metal species.

3. A device as claimed in claim 2 wherein, said sequestration medium comprises a mixture of a metal complexing agent and a long chain organic acid.

4. A device as claimed in claim 3 wherein said complexing agent comprises a complexing agent selected from the group consisting of quinolines, dithiocarbamates, polyamines, iminodiacetate, polyketones, and thiols and said organic acid comprises an organic acid selected from the group consisting of oleic acid, steric acid, eladic acid, linoleic acide, and linolenic acid.

5. A device as claimed in claim 4 wherein said complexing agent comprises alkyl substituted 8-hydroxy quinolines.

6. A device as claimed in claim 5 wherein said quinolines comprise 7-(4-ethyl-1-methyloctyl)-8-hydroxy quinoline and said organic acid comprises oleic acid.

7. A device as claimed in claim 1 wherein the nonporous membrane forms a sealed tube and said sequestration media is contained within the tube.

8. A device as claimed in claim 7 wherein said tube comprises a flattened tube.

9. A device as claimed in claim 7 further comprising a microporous polymer surrounding the tube formed by the nonporous membrane.

10. A device as claimed in claim 7 wherein said nonporous polymeric membrane comprises a nonporous synthetic polymer selected from the group consisting of polyethylene, polypropylene, silicone, polyvinylchloride, chlorinated polyethylene, chlorosuphonated polyethylenes, polyimides, and polyethylene vinylacetate copolymers.

11. A device as claimed in claim 10 wherein membrane comprises a said synthetic nonporous polymer laminated with a microporous polymer.

12. A device as claimed in claim 7 wherein said nonporous membrane has a thickness between 2 and 500 $\mu$m.

13. A device as claimed in claim 7 further comprising a sheath for permitting movement of water and associated ionic metal species to membrane surface sites at which reaction with the sequestration phase occurs while limiting water flow past said membrane surface sites.

14. A device as claimed in claim 13 wherein said sheath comprises a hydrophilic polymer membrane.

15. A device as claimed in claim 13 wherein said sheath comprises a hydrophilic membrane selected from the group consisting of cellulose dialysis membranes, and hydrophilic polypropylene, polyvinylidene fluoride and polyether sulphone polymer membranes.

16. A device for removing and concentrating ionic metal species from water, said device comprising:
    a nonporous polymeric tube for capturing ionic metal species dissolved in water, said tube being comprised of a membrane having a transient cavities therein having average size no greater than 10 Å; and
    a sequestration medium contained within said tube for transforming the ionic metal species captured by said tube into a complexed, non-mobile metal species, said sequestration medium comprising a medium capable of diffusing through the nonporous polymeric membrane at a controlled rate and of forming said complexed, non-mobile species.

17. A device as claimed in claim 16 wherein, said sequestration medium comprises a mixture of a metal complexing agent and a long chain organic acid.

18. A device as claimed in claim 17 wherein said complexing agent comprises a complexing agent selected from the group consisting of quinolines, dithiocarbamates, polyamines, iminodiacetate, polyketones, and thiols and said organic acid comprises an organic acid selected from the group consisting of oleic acid, steric acid, eladic acid, linoleic acide, and linolenic acid.

19. A device as claimed in claim 16 further comprising a microporous polymer surrounding the tube formed by the nonporous membrane.

20. A device as claimed in claim 16 further comprising a sheath for permitting movement of water and associated ionic metal species to membrane surface sites at which reaction with the sequestration phase occurs while limiting water flow past said membrane surface sites.

* * * * *